(12) United States Patent
Bonnin et al.

(10) Patent No.: US 10,001,663 B2
(45) Date of Patent: Jun. 19, 2018

(54) METHOD OF DETERMINING AT LEAST ONE PARAMETER OF VISUAL BEHAVIOUR OF AN INDIVIDUAL

(71) Applicant: ESSILOR INTERNATIONAL (COMPAGNIE GENERALE D'OPTIQUE), Charenton-le-Pont (FR)

(72) Inventors: Thierry Bonnin, Charenton-le-Pont (FR); Guilhem Escalier, Charenton-le-Pont (FR); Ahmed Haddadi, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days. days.

(21) Appl. No.: 15/312,526

(22) PCT Filed: May 19, 2015

(86) PCT No.: PCT/FR2015/051314
§ 371 (c)(1),
(2) Date: Nov. 18, 2016

(87) PCT Pub. No.: WO2015/177459
PCT Pub. Date: Nov. 26, 2015

(65) Prior Publication Data
US 2017/0090220 A1    Mar. 30, 2017

(30) Foreign Application Priority Data
May 20, 2014    (FR) .................................... 14 54547

(51) Int. Cl.
*A61B 3/10* (2006.01)
*G02C 13/00* (2006.01)
(Continued)

(52) U.S. Cl.
CPC ............ *G02C 13/005* (2013.01); *A61B 3/113* (2013.01); *A61B 3/14* (2013.01)

(58) Field of Classification Search
CPC .... G02C 13/005; G02C 13/003; G02C 7/027; A61B 3/111; A61B 3/0025
(Continued)

(56) References Cited

U.S. PATENT DOCUMENTS

| | | | |
|---|---|---|---|
| 9,726,911 B2 * | 8/2017 | Encaoua | G02C 13/003 |
| 2009/0040460 A1 | 2/2009 | Bonnin et al. | |
| 2009/0214086 A1 * | 8/2009 | Thomet | A61B 3/032 382/117 |
| 2010/0118123 A1 | 5/2010 | Freedman et al. | |

(Continued)

FOREIGN PATENT DOCUMENTS

| | | | |
|---|---|---|---|
| FR | 2 914 173 A1 | 10/2008 | |
| FR | 2 932 675 A1 | 12/2009 | |

(Continued)

OTHER PUBLICATIONS

International Search Report, dated Sep. 4, 2015, from corresponding PCT Application.

*Primary Examiner* — Mohammed Hasan
(74) *Attorney, Agent, or Firm* — Young & Thompson

(57) ABSTRACT

Disclosed is a method of determining at least one visual behavior parameter of an individual, including: determination of the position of the center of rotation of at least one eye of the individual in a first reference frame tied to the head of the individual; capture, with the aid of an image capture device, of at least one image of at least one part of the body of the individual in a second reference frame, determination of the position and the orientation, in the second reference frame, of the first reference frame tied to the head of the individual, by searching for the position, in the second reference frame of a distinctive zone of the part of the body of the individual; determination of the position of the center of rotation of the eye in the second reference (Continued)

frame; and determination of the sought-after visual behavior parameter.

20 Claims, 1 Drawing Sheet

(51) Int. Cl.
    *A61B 3/14*     (2006.01)
    *A61B 3/113*     (2006.01)

(58) Field of Classification Search
    USPC .................................................. 351/200–246
    See application file for complete search history.

(56) References Cited

U.S. PATENT DOCUMENTS

| | | |
|---|---|---|
| 2010/0128220 A1 | 5/2010 | Chauveau |
| 2012/0033178 A1 | 2/2012 | Chauveau et al. |
| 2012/0321134 A1 | 12/2012 | Shen et al. |
| 2016/0291349 A1* | 10/2016 | Koh ........................ G02C 11/10 |
| 2017/0188807 A1* | 7/2017 | Swital .................. A61B 3/0025 |

FOREIGN PATENT DOCUMENTS

| | | |
|---|---|---|
| WO | 2006/106248 A1 | 10/2006 |
| WO | 2010/119190 A1 | 10/2010 |

* cited by examiner

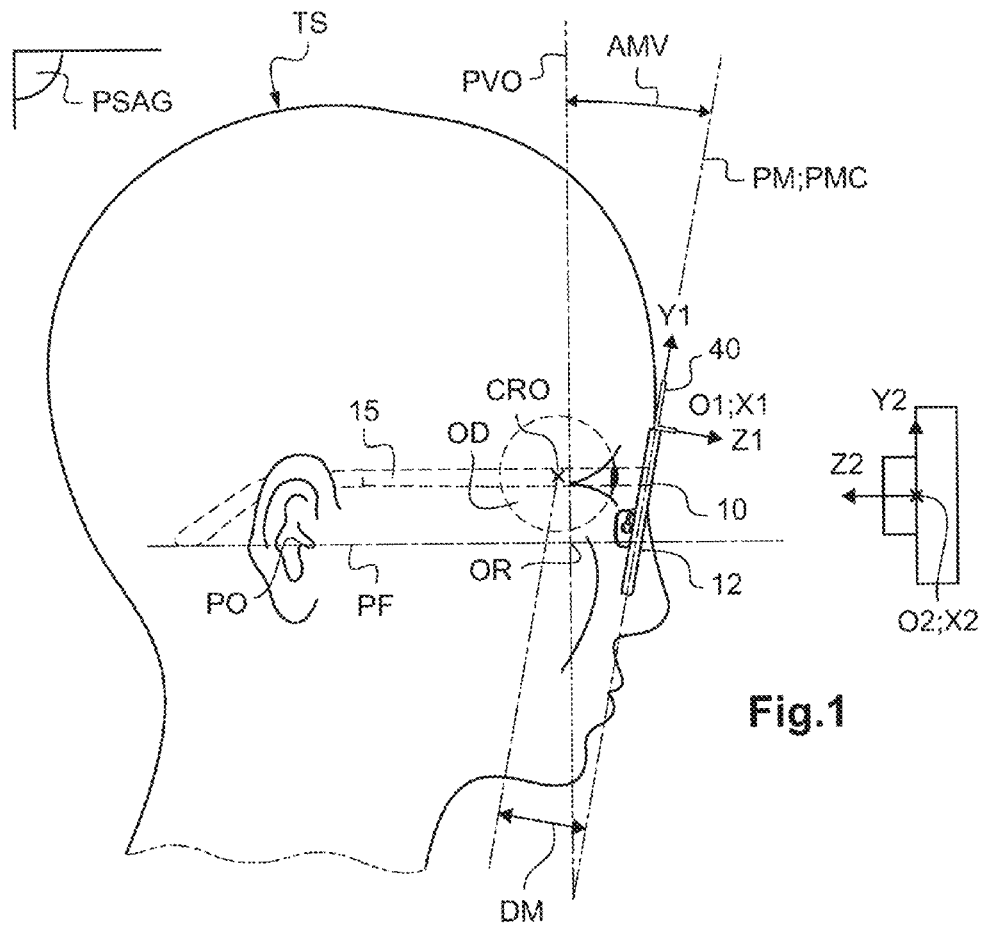
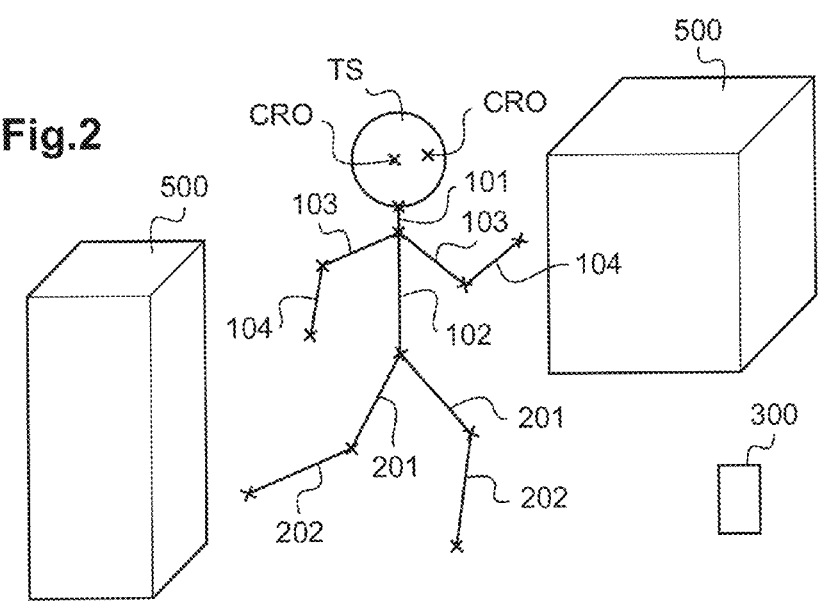

METHOD OF DETERMINING AT LEAST ONE PARAMETER OF VISUAL BEHAVIOUR OF AN INDIVIDUAL

TECHNICAL FIELD OF THE INVENTION

The present invention relates to the field of personalization of ophthalmic lenses intended to be fitted in a spectacle frame.

It more precisely relates to a method for determining at least one parameter of visual behavior of an individual.

PRIOR ART

Methods allowing the ophthalmic lenses of a piece of optical equipment intended for an individual to be personalized depending on parameters associated with the individual and the spectacle frame chosen thereby are known.

Such a method is for example based on the determination of the position of the rotation center of each eye of the individual with respect to the frame positioned on his head. It is then possible to precisely determine the position of the optical center of each ophthalmic lens in the chosen frame so that the ophthalmic lens is correctly positioned in front of the eyes of the individual.

Here, the position of the rotation center of the eye is determined with respect to the ophthalmic lens, statically, under conditions that are very different from the natural conditions under which the frame is worn, without taking into account the posture of the individual.

Known methods do not allow, for example, the position of the rotation center of the eye of the individual to be determined with respect to the posture of the body of the individual, under conditions similar to those encountered in the day-to-day life of the individual and possibly during a movement of this individual.

Specifically, existing methods and devices that allow the posture of the body to be determined with respect to the image-capturing device are not precise enough to allow the position of the rotation centers of the eyes to be determined with respect to the body.

SUBJECT OF THE INVENTION

In order to remedy the aforementioned drawbacks of the prior art, the present invention proposes a method for determining at least one parameter of visual behavior of an individual allowing the posture of the body of the individual to be taken into account.

More particularly, according to the invention a method for determining at least one parameter of visual behavior of an individual is proposed, this method comprising the following steps:
- determining the position of the rotation center of at least one eye of the individual in a first frame of reference associated with the head of the individual,
- capturing, using an image-capturing device, at least one image of at least one portion of the body of the individual in a second frame of reference,
- determining the position and orientation, in the second frame of reference, of the first frame of reference associated with the head of the individual, by seeking the position, in the second frame of reference, of a recognizable zone of said portion of the body of the individual,
- determining the position of the rotation center of the eye in the second frame of reference,
- determining the sought parameter of visual behavior.

It is thus possible to personalize the ophthalmic lenses intended for the spectacle frame chosen by this individual depending on this parameter of visual behavior.

It will be noted that the parameter of visual behavior is determined in the second frame of reference, for example in a context in which the individual is behaving more naturally; this determination may however thus use the position of the rotation center of the eye (in the second frame of reference) initially determined with precision in the first frame of reference, for example in a professional environment.

For the capturing step, the individual is for example placed in a real-life situation in which the posture of the head and body of the individual is unconstrained.

The parameter of visual behavior is thus determined, while taking into account the position of the rotation center of the eye, in the second frame of reference in which the posture of the head and the body of the individual correspond to that which he adopts naturally, in the real-life situation in question.

Moreover, the position and/or orientation of the recognizable zone of said portion of the body of the individual are for example predetermined in the first frame of reference, thereby allowing, on the basis of the image captured in the second frame of reference, the relative position of the first frame of reference and the second frame of reference to be obtained.

The following are other nonlimiting and advantageous features of the method according to the invention:
- in the step of determining the position of the rotation center in the first frame of reference, the position of the rotation center of the eye of the individual is determined from a morphological database of the individual;
- in the step of determining the position of the rotation center in the first frame of reference, the position of the rotation center of the eye of the individual is determined from one or more acquisitions of images of the head of the individual;
- in the capturing step, said image is a three-dimensional representation of the portion of the body of the individual or of the head of the individual;
- in the capturing step, a sequence of images is preferably captured during a predetermined duration, and, in the step of determining the sought parameter of visual behavior, the variation in the sought parameter of visual behavior during this predetermined duration is deduced therefrom;
- in the capturing step, at least one sequence of ten images is captured while the movements of the individual are unconstrained;
- in the step of determining position and orientation, said recognizable zone consists of a pinpointing device mounted on the head of the individual, of a spectacle frame placed on the head or of one or more recognizable points of the face of the individual;
- in the step of determining the sought parameter of visual behavior, the direction of the gaze of the individual in said real-life situation is determined, and a zone of use of the ophthalmic lens corresponding to this real-life situation is determined therefrom;
- to determine the direction of the gaze of the individual, the image of the pupil of the individual is identified in the image captured in the capturing step, and the sought direction of the gaze is deduced therefrom depending on the position of the rotation center in the first frame of reference, said position being determined in the step of determining the position of the rotation center in the first frame of reference;

to determine the direction of the gaze of the individual, the position in the second frame of reference of elements targeted by the gaze and belonging to the environment of the individual is determined;

said elements targeted by the gaze are displayed on an electronic screen and have a known position with respect to the image-capturing device;

in the step of determining the position of the rotation center in the first frame of reference,
    at least two images of the head of the individual are captured using an image-capturing device, in which images the postures of the head of the individual with respect to this image-capturing device are different and in which images the individual is fixating his gaze on a sighting point of predetermined position,
    the gaze directions of the individual corresponding to each of the two images are determined,
    the position of the rotation center of the eye of the individual is deduced therefrom;

the aforementioned real-life situation is one of the following real-life situations:
    reading and/or writing situations,
    rest situations,
    walking on foot situations,
        situations in which the individual is climbing or descending a staircase;

in the capturing step, the image-capturing device is placed such that the moving individual retains a substantially three-quarter orientation with respect to this image-capturing device in the corresponding real-life situation;

in the step of determining the position of the rotation center in the first frame of reference, the head of the individual is equipped with a pair of spectacles surmounted by a pinpointing system, in the capturing step, the captured portion of the body comprises the head of the individual equipped with this pinpointing system, and, in the step of determining the position and orientation, the recognizable zone consists of this pinpointing system;

the sought parameter of visual behavior of the individual is one of the following:
    a zone of use corresponding to the real-life situation for a corrective lens to be placed in a spectacle frame intended to equip the head of the individual,
        a behavioral parameter of the individual specifying whether he moves his eyes or head more,
    average reading distance,
    natural posture of the individual at rest,
    dynamic behavior of the eyes during the chosen real-life situation,
    position of a near-vision zone or progression length or inset of a corrective lens to be placed in a spectacle frame intended to equip the head of the individual,
    the pantoscopic angle of a corrective lens to be placed in a spectacle frame intended to equip the head of the individual determined so as to decrease the astigmatic aberrations;

the steps of determining the position of the rotation center in the first frame of reference and of capturing are carried out in one and the same place, using one and the same image-capturing device;

the steps of determining the position of the rotation center in the first frame of reference and of capturing are carried out in two different places, using two different image-capturing devices;

at least the capturing step is carried out by the individual in his usual environment.

DETAILED DESCRIPTION OF AN EXEMPLARY EMBODIMENT

The description which follows with regard to the appended drawings, given by way of nonlimiting examples, will clearly elucidate the gist of the invention and how it may be embodied.

In the appended drawings:

FIG. 1 is a schematic profile view of the head of the individual during an image capture in step a) of the method according to the invention, and FIG. 2 is a schematic view of the body of the individual during an image capture in step c) of the method according to the invention.

The method according to the invention includes the following steps:

a) the position of the rotation center of at least one eye of the individual in a first frame of reference associated with the head of the individual is determined, b) the individual is placed in a real-life situation in which the posture of the head and body of the individual is unconstrained, c) at least one image of at least one portion of the body of the individual is captured using an image-capturing device, d) depending on the image captured in step c), the position and orientation of said portion of the body of the individual is determined in a second frame of reference, e) the position and orientation, in the second frame of reference, of the first frame of reference associated with the head of the individual is determined by seeking the position, in the second frame of reference, of a recognizable zone of said portion of the body of the individual, the position and orientation of which in the first frame of reference are predetermined, f) the position of the rotation center of the eye in the second frame of reference are deduced therefrom, g) the sought parameter of visual behavior is deduced therefrom.

In practice, the method is implemented by a computational processing unit.

This computational processing unit makes use of the position of the rotation center of at least one eye of the individual in the first frame of reference associated with the head of the individual, which position is present in a memory of this processing unit and transmitted to this processing unit or indeed determined by the processing unit from measurements carried out on the individual, especially two-dimensional or three-dimensional images of the head of this individual captured in step a) by a first device for capturing two-dimensional or three-dimensional images.

It also makes use of other measurements carried out on the individual, comprising at least one two-dimensional or three-dimensional image of a portion of the body of the individual, said image being captured in step c) with a second image-capturing device that may be the same as that used possibly in step a).

By portion of the body, what is meant is a portion of the body comprising at least one portion other than the head of the individual. More precisely, it is preferably a question of a portion of the body located below the shoulder line of the individual.

This portion of the body may include the head of the individual. It furthermore preferably includes the neck and/or a portion of the chest of the individual.

It may include all of the body and head of the individual, as explained below.

From the two- or three-dimensional images obtained in step c), the computational processing unit determines the posture of said portion of the body in the second frame of reference, i.e. the position and orientation of this portion of the body in the second frame of reference.

This second frame of reference may be a frame of reference associated with the image-capturing device or an absolute spatial frame of reference, or a frame of reference associated with an element of the environment of the individual.

Next, the computational processing unit is programmed to reposition the first frame of reference associated with the head of the individual with respect to the second frame of reference, so as to allow the position of the rotation centers of the eyes of the individual with respect to the portion of the body of the individual to be determined.

The computational processing unit then deduces therefrom at least one parameter of visual behavior of the individual. By virtue of the preceding steps, this determination takes into account the posture of the body and of the head of the individual in its real-life situation.

The various steps will now be described in more detail.

Step a)

In this step, the position of the rotation center CRO of at least one eye OD of the individual is determined in the first frame of reference associated with the head TS of the individual, by any technique known to those skilled in the art.

The head of the individual TS is for example shown in FIG. 1.

The Frankfurt plane PF of the head TS of the individual is defined as the plane passing through the lower orbital points OR and the porion PO of the individual, the porion being the highest point in the skull of the auditory canal, which corresponds to the tragion of the ear.

The Frankfurt plane PF is horizontal in an orthostatic position, in which position he makes a minimum of effort. The gaze axis of the individual is then the primary gaze axis, i.e. he is gazing straight ahead.

A sagittal plane PSAG of the head TS of the individual is defined as being the vertical plane passing through the perpendicular bisector of the two eyes. The perpendicular bisector of the eyes is the axis passing through the middle of the segment defined by the rotation centers of the two eyes, perpendicular to this segment, and parallel to the Frankfurt plane PF.

Preferably, this rotation center is determined from a measurement carried out on the face of the individual.

This measurement may especially comprise capturing one or more two-dimensional images of the head of the individual or acquiring one or more three-dimensional representations of the head of the individual by virtue of a first image-capturing device.

It is here preferably a question of capturing an image or acquiring a representation having a high resolution, for example at least 640×480 (VGA).

Thus, according to a first embodiment of step a), the position of the rotation center CRO of the eye is determined from two two-dimensional images of the head of the individual in two different cephalic postures for one given gaze direction with respect to the first image-capturing device used to capture these images.

The principle of this determination is for example described in detail in document FR2914173, an equivalent of which in English is the document US20100128220.

In particular, according to this first embodiment of step a),
at least two images of the head of the individual are captured using the first image-capturing device, in which images the postures of the head of the individual with respect to the first image-capturing device are different and in which images the individual is fixating his gaze on a sighting point of predetermined and fixed position,
the gaze directions of the individual corresponding to each of the two images are determined,
the position of the rotation center of the eye of the individual in the first frame of reference associated with the head of the individual is deduced therefrom.

The captured images of the head of the individual are transmitted to the computational processing unit.

The captured images may be processed in real-time or after all the images have been captured.

From these images captured in step a), the computational processing unit determines the position of the rotation center CRO of at least one eye of the individual in the first frame of reference associated with the head of the individual.

By way of example, it is possible to identify the images of a recognizable point of the eye of the individual, for example the pupil of the eye of the individual, in two images captured while the individual is fixating his eyes on a target the position of which with respect to the first image-capturing device is different for each captured image.

The position of the target fixated with the gaze during the two image captures being known relative to the first image-capturing device, the position of the eye rotation center CRO is deduced therefrom as being the intersection of the straight lines passing through the target and the pupil of the eye for each captured image.

It is also possible to determine for each gaze direction, the corresponding posture of the head of the individual, i.e. its position and its orientation in a frame of reference associated with the first image-capturing device. A data pair associating the posture of the head and the gaze direction is stored in correspondence with the image.

In practice, the first image-capturing device is then preferably a camera or video camera. It is for example securely fastened to a display screen on which said targets forming the sighting points are displayed. It may for example be a question of a tablet including a video camera that constitutes the first image-capturing device. The targets may comprise either a plurality of static images appearing at various locations on the screen, or a dynamic image moving across the screen.

The individual may optionally be equipped with a spectacle frame 10 and/or a pinpointing system 40 intended to allow the position of the head of the individual in space to be determined from a captured image of the head of the individual equipped with the pinpointing system. This pinpointing system is described in detail in document FR2914173, page 7, line 5 to page 10, line 8. It will therefore not be described in more detail here.

The frame 10 may be full-rimmed or rimless. In the example shown in FIG. 1, it is full-rimmed and therefore includes two rims 12 connected by a bridge and intended to accommodate the ophthalmic lenses, and two frame temples 15 that are intended to rest on the ears of the individual.

The pinpointing system 40 has predetermined geometric characteristics, which allow, from a captured image of the head of the individual, in which image this pinpointing system appears, the position and the orientation of the head of the individual in space to be determined in said frame of reference associated with the image-capturing device. This pinpointing system therefore allows the position and orientation of the first frame of reference associated with the head of the individual to be determined in the frame of reference associated with the image-capturing device.

The first frame of reference (O1, X1, Y1, Z1) associated with the head of the individual may moreover be associated with the pinpointing system 40, as schematically shown in FIG. 1. In this example, the center of the frame of reference is placed in the middle of the pinpointing system, which is located in the sagittal plane of the head of the individual. The axis (O1,Y1) extends in the midplane of the frame PM, which is here coincident with the midplane of each rim PMC.

The axis (O1, X1) is parallel to the segment connecting the rotation centers of the eyes of the individual and the axis (O1, Z1) is perpendicular to the two axes (O1, X1) and (O1, Y1).

The geometric characteristics of the pinpointing system 40 give access to a scale factor of each captured image and to the rotation angles of the head of the individual with respect to the image-capturing device.

An example of a frame of reference (O1, X2, Y2, Z2) associated with the image-capturing device is shown in FIG. 1 in the case where it is a question of a video camera or camera. The center O2 of this frame of reference is for example placed in the center of the sensor of this device. The axis (O2, Z2) extends along the optical axis. The axes (O2, Y2) and (O2, X2) extend in the plane perpendicular to the optical axis.

According to a second embodiment of step a), the position of the eye rotation center CRO is determined depending on a predetermined average position of this rotation center.

It may for example be a question of its average position with respect to the back face of an ophthalmic lens fitted in a spectacle frame placed on the head of the individual. To this end, the rotation center may for example be considered to be located at an average distance DM equal to 27 millimeters from the back face of the ophthalmic lens. It is thus possible to determine the position of the rotation center from a captured two-dimensional profile image of the head of the individual (see for example FIG. 1).

According to a third embodiment of step a), the three-dimensional coordinates of the rotation centers of the eyes are determined from three-dimensional images of the head of the individual.

In the case of three-dimensional images, three-dimensional representations will also be spoken of below.

In practice, the implementation of this second embodiment is similar to that of the first embodiment.

For example, at least two three-dimensional representations of the head of the individual are acquired while the latter fixates his gaze on a target the position of which with respect to said first image-capturing device is known and for different angles of the head with respect to the first image-capturing device.

This first image-capturing device is here a device for acquiring the three-dimensional representation.

The target is for example located straight in front of the individual.

For each three-dimensional representation, the position of the pupil of the eye of the individual is determined and the direction of the gaze is determined as the straight line connecting the pupil to the target.

By superposing the two representations, the rotation center of the eye is determined as the intersection between the two determined gaze directions.

The rotation centers of the eyes of the individual may thus be pinpointed by their coordinates in a frame of reference associated with the first device for acquiring the three-dimensional representation.

These coordinates may then be transposed to the first frame of reference associated with the head of the individual.

The first frame of reference may be associated with a spectacle frame placed beforehand on the head of the individual, with particular points of the face of this individual, or even with a pinpointing system of the type described in document FR2914173.

The three-dimensional representations may be obtained by a stereoscopic image-capturing technique, or by a three-dimensional acquiring technique such as a three-dimensional scanning technique, which is for example based on structured light.

The latter devices for acquiring a three-dimensional representation comprise means for projecting structured light, for example including a pattern such as a moiré pattern, onto the head of the individual while the image-capturing means record one or more two-dimensional images of the head of the individual. Since the pattern is known, processing of these images allows the three-dimensional representation to be determined.

These three-dimensional representations may also be obtained by a plenoptic imaging method. It is a question of a multi-focal imaging method allowing a plurality of viewpoints to be captured with a single sensor. This type of image (called a light-field image) allows a three-dimensional representation of the head of the individual to be determined.

According to a fourth embodiment of step a), the position of the rotation center of the eye of the individual is determined from a database of morphological data of the individual.

In this case, in step a), a dataset relating to the individual and for example originating from the processing of images or of three-dimensional representations recorded beforehand, is recovered and exploited by the computational processing unit to determine the position of the rotation centers.

Generally, it is possible to envision step a) being carried out either by a person specialized in optometry, such as an optician, using a dedicated device, or by the individual himself, without intervention by a person specialized in optometry and/or using a commonly available device.

It is for example carried out at an opticians, with the dedicated means possessed thereby, and under the particular conditions associated with the workplace of the optician, especially in terms of the positioning of the individual, lighting, measuring devices and the short time dedicated to the measurement.

Step b)

The individual is placed in a real-life situation in which the posture of the head and body of the individual is unconstrained.

It is in particular a question of one of the following real-life situations:
reading and/or writing situations,
rest situations,
walking on foot situations, situations in which the individual is climbing or descending a staircase.

The reading/writing situations, in which the individual is seated on a chair, stool or sofa in front of a desk, are intended to allow reading distances and a cephalic carriage (defined by a lowering angle and a roll angle) or an angle of inclination of the head during a reading task, to be determined.

The rest situations allow an overall bodily posture to be determined, this posture possibly influencing the vision parameters. It is in particular important to determine whether the individual has a bent or straight posture at rest.

A plurality of dynamic situations such as walking and climbing and/or descending staircases for example allow oscillation or hesitation behaviors of the individual to be observed.

In step b), the individual is preferably in his normal environment, i.e. for example in his home, at his desk, in his car or on foot in his own neighborhood.

However, it is also possible to envision, in step b), the individual being in the shop of the optician. Provision may then be made for various real-life situations to be simulated in the shop of the optician, the individual for example being asked to sit to read or watch a screen on a sofa or to climb or descend a staircase.

Step c)

At least one image of at least one portion of the body of the individual is captured using a second image-capturing device. It may be a question of two- or three-dimensional images. In the case of three-dimensional images, three-dimensional representations will also be spoken of.

When a first device for capturing two- or three-dimensional images is used in step a), the second image-capturing device used in step c) may be that of step a) or distinct from that of step a). The device may optionally be used in a different acquiring mode (multiresolution) in the two cases.

Preferably, the two- or three-dimensional image captured in step c) comprises at least two-dimensional images or three-dimensional representations of the head of the individual and of a portion of his chest.

Preferably, this image comprises the whole body with the head of the individual.

According to a first embodiment of step c), said image is a three-dimensional representation of the portion of the body of the individual.

The three-dimensional representations may be obtained, as in step a), by a stereoscopic image-capturing technique, or by a three-dimensional acquiring technique such as a three-dimensional scanning technique, which is for example based on structured light.

The second image-capturing device is then a device for acquiring a three-dimensional representation comprising means for projecting structured light, i.e. light having a pattern such as a moiré pattern, onto the head of the individual while the image-capturing means record one or more two-dimensional images of the head of the individual. Since the pattern is known, processing of these images allows the three-dimensional representation to be determined.

A device such as the "Kinect", the operating principle of which is described in document US20100118123, may for example be used.

These three-dimensional representations may also be obtained by a plenoptic imaging method. It is a question of a multi-focal imaging method allowing a plurality of viewpoints to be captured with a single sensor. This type of image (called a light-field image) allows a three-dimensional representation of the body of the individual to be determined.

According to a second embodiment of step c), said image captured in step c) is a two-dimensional image captured using a second image-capturing device such as a camera or video camera.

Whatever the envisaged embodiment, the orientation of the individual with respect to the second image-capturing device allows the gaze of the individual and the environment of the individual to be observed. For example, in the case where the task of the individual consists in climbing or descending staircases, it is necessary to be able to observe the posture of the head and of the body of the individual and the stairs of the staircase.

The ideal posture most often corresponds to an orientation of the body and head of the individual such that three quarters of the latter is seen by the second image-capturing device.

The second image-capturing device is then preferably placed such that the moving individual retains a substantially three-quarter orientation with respect to this second image-capturing device in the corresponding real-life situation.

In practice, the three-quarters posture implies that the sagittal plane of the head of the individual will be oriented at an angle comprised between 20 and 50 degrees to a plane perpendicular to the image-capturing plane of the second image-capturing device, in the case where a second image-capturing device captures two-capturing dimensional images.

Furthermore, in step c), a sequence of two- or three-dimensional images is preferably captured during a predetermined duration.

More precisely, at least one sequence of ten images is captured while the movements of the individual are unconstrained.

It is possible to envision step c) being carried out either by a person specialized in optometry, such as an optician, using a dedicated device, or by the individual himself, without intervention by a person specialized in optometry and/or using a commonly available device.

It is for example carried out at an opticians, with the dedicated means possessed thereby, and under the particular conditions associated with the workplace of the optician, especially in terms of the positioning of the individual, lighting, measuring devices and the short time dedicated to the measurement.

In practice, in order to capture the two- or three-dimensional images in step c), the individual then follows a measuring protocol announced by the optician.

As a variant, step c) is carried out by the individual himself, in the normal environment of the individual, using commonly available measuring devices such as a camera, a video camera or a webcam, it then being possible to devote much more time thereto than is dedicated to the measurements generally carried out at an opticians.

In practice, in order to capture the two- or three-dimensional images of step c), the individual then follows a measuring protocol that may be announced by a leaflet explaining the protocol to be followed or an Internet site explaining to the individual how to carry out the measurement. In each step of this measuring protocol, the individual may be asked to interact with the second image-capturing device used.

Step d)

Depending on the image captured in step c), the position and orientation of said portion of the body of the individual is determined in a second frame of reference.

This second frame of reference may be associated with said second image-capturing device or an absolute frame of reference, or associated with the environment of the individual, which is not associated with the first image-capturing device.

This step is carried out by the computational processing unit on the basis of the two- or three-dimensional images captured in step c).

It is a question of determining a three-dimensional model of said portion of the body of the individual.

Specifically, in the case where the three-dimensional representation of the body of the individual in step c) is acquired by virtue of a "Kinect" device 300 (FIG. 2), it is possible, as is known, to process the three-dimensional representations acquired so as to ascertain the positions and angles of certain segments 101, 102, 103, 104, 201, 202 of the body, said segments being defined beforehand by the user.

In the case of a Kinect module for example, the pinpointed segments of the body are defined and modelled in the OpenNI module.

On the whole, the second acquiring device gives the position and orientation of the portions of the body in space. It allows the movement of the body of the individual to be followed in real time in a quite large volume of space.

The resolution is about 0.5 centimeters. This resolution especially allows the pinpointing system placed on the head of the individual for example to be identified.

As is schematically shown in FIG. 2, the following segments of the body are for example defined: the neck 101, the chest 102, the arms 103, the forearms 104, the thighs 201, the legs 202 and optionally the hands and feet.

Each segment comprises at least one end associated with a joint of the body and possessing at least one degree of freedom with respect to the neighboring segment.

For example, it is especially possible to take as reference system the following 4 points: the left acromion (LAC), the right acromion (RAC), the manubrium (SJN) and the xiphoid process (SXS). In the case of use of a Kinect module, the following points are for example used: SHOULDER_RIGHT, SHOULDER_LEFT, SPINE_SHOULDER, SPINE_MID.

The position of the joints of the individual and the angles of the determined segments allow a three-dimensional model of said portion of the body of the individual to be established.

In FIG. 1, the environment of the individual is schematically represented by the reference elements 500.

Step e)

The position and orientation, in the second frame of reference, of the first frame of reference associated with the head of the individual are determined by seeking the position, in the second frame of reference, of a recognizable zone of said portion of the body of the individual, the position and orientation of which in the first frame of reference are predetermined.

This recognizable zone for example consists of a plurality of recognizable points associated with said portion of the body of the individual.

This recognizable zone may consist of the neck of the individual.

Specifically, the neck may be visible in the image of the head of the individual captured in step a) and in the image of the portion of the body of the individual captured in step c).

The recognizable points of the recognizable zone may also be associated with the aforementioned pinpointing system mounted on the head of the individual as mentioned above, with a spectacle frame placed on the head of the individual or with one or more recognizable points of the face of the individual.

Thus, preferably, in step a) the head of the individual is equipped with a pair of spectacles surmounted by a pinpointing system, in step c) the captured portion of the body comprises the head of the individual equipped with this pinpointing system, and in the step e) the recognizable zone consists of this pinpointing system.

The method called the "PostIt method" published by Daniel F. DeMenthon and Larry S. Davis in May 1995 may be used for this purpose. This method allows the position and/or orientation of an object to be found from a single two-dimensional image and a three-dimensional model of the object.

The implementation of this method requires at least 4 points of correspondence between the two-dimensional object and the three-dimensional model to be found. These points of correspondence are for example recognizable points of the pinpointing system placed on the head of the individual in steps a) and c). The three-dimensional model is that of the body of the individual and the two-dimensional object corresponds to the positions of the rotation center of the eye in the first frame of reference. The reader may for example refer to document US2012/321 134.

It is here in fact a question of placing the rotation centers of the eyes of the individual in the three-dimensional second frame of reference of step c), so as to determine the position of these rotation centers with respect to the body of the individual.

Step f)

Once the first frame of reference has been positioned with respect to the second frame of reference, the position of the rotation center of the eye in said second frame of reference is determined.

It is here a question of a step of changing frame of reference.

Step g)

The parameter of visual behavior of the individual determined in step g) is for example one of the following:
- a zone of use corresponding to the real-life situation of step b) for a corrective lens to be placed in a spectacle frame intended to equip the head of the individual,
- a behavioral parameter of the individual specifying whether he moves his eyes or head more during a determined visual task,
- an average reading distance,
- a natural posture of the individual at rest,
- a dynamic behavior of the eyes during the chosen real-life situation,
- a position of a near-vision zone or progression length or inset of a corrective lens to be placed in a spectacle frame intended to equip the head of the individual,
- the pantoscopic angle AMV of a corrective lens to be placed in a spectacle frame intended to equip the head of the individual determined so as to decrease the astigmatic aberrations.

The pantoscopic angle AMV is defined as the angle between the midplane of each rim PMC of the spectacle frame and the vertical eye plane PVO, which is the plane perpendicular to the Frankfurt plane passing through the rotation centers CRO of the eyes, measured in projection in the sagittal plane of the head of the individual.

For example in step g), the direction of the gaze of the individual in said real-life situation is determined, and a zone of use of the ophthalmic lens corresponding to this real-life situation is determined therefrom.

The zone of use of the ophthalmic lens is defined as being a zone of space representative of a statistical distribution of a set of points on the lens through which the gaze of the individual passes during a particular visual task, or for a use at a predetermined working distance. The zone of use may be defined equivalently either spatially, by a statistical distribution of points over the ophthalmic lens or over another projection plane associated with the ophthalmic lens or with the rim of the corresponding frame, or vectorially, by a statistical distribution of directions of the gaze. Alternatively and more simply, the zone of use ZU may also be defined in tabulated format by a statistical distribution of the lowering angles of the gaze in the sagittal plane of the individual.

The lowering angle of the gaze is defined as the angle between the gaze direction and a predetermined primary gaze direction in projection in the sagittal plane of the head of the individual.

This predetermined primary gaze direction corresponds to the gaze direction of the individual under far-vision conditions, i.e. under conditions such that the individual fixates on a point that is at a distance of at least 5 meters therefrom.

To determine the direction of the gaze of the individual, the image of the pupil of the individual is identified in the two- or three-dimensional image captured in step c), and the sought direction of the gaze is deduced therefrom. The gaze direction is therefore determined depending on the position of the rotation center of the eye in the first frame of reference, which position is determined in step a).

More precisely, this gaze direction is determined as the straight line connecting the rotation center of the eye and the pupil of this eye.

As a variant, an eye tracker could be used.

By virtue of step d), it is possible to define this gaze direction in the first or second frame of reference.

It is possible to envision, to determine the direction of the gaze of the individual, determining the position, in the second frame of reference, of elements targeted by the gaze and belonging to the environment of the individual. The elements targeted by the gaze in question are for example displayed on a display screen and have a known position with respect to the second image-capturing device.

These targeted elements may thus consist of a display screen, staircase stairs, the pages of a book, or any element of the environment of the individual.

The direction of the gaze may then be determined as the straight line connecting the rotation center of the eye and the targeted element fixated on by the gaze of the individual.

Next, the intersection of the direction of the gaze and a midplane of the ophthalmic lens, which is intended to be placed in front of the eye of the individual, is for example determined.

The midplane of the ophthalmic lens may optionally be approximated by the midplane of the rim of the corresponding frame.

The position and orientation of the midplane of the lens are for example predetermined in a calibrating step.

This determination may take into account the shape of the spectacle frame chosen by the individual. To replace the midplane of the lens, it is also possible to use the front or back face of the lens, or a mid-surface equidistant from this front and back face.

In the case where the ophthalmic lens in question is a progressive lens, the determined zone of use may in particular consist of the near- or far-vision zone of the progressive ophthalmic lens.

The power of the progressive ophthalmic lens varies, preferably continuously, between a far-vision reference point located in the zone of use of the lens used for far vision and a near-vision reference point located in the zone of use used for near vision, along a curve called the "principal progression meridian curve" that passes between these two points. This principal progression meridian curve passes through these two zones of use and an intermediate zone of use located between the zone of near-vision use and the zone of far-vision use, in an overall vertical direction.

The progression length and/or the inset of the progressive ophthalmic lens may also advantageously be deduced depending on this zone of near- and/or far-vision use.

The progression length of the ophthalmic lens is defined as the vertical distance between the fitting cross and the position of the near-vision reference point defined by the manufacturer of the eyeglass.

The fitting cross is a reference point for positioning the lens in front of the eye of an individual and the position of which is predefined by the manufacturer of the lens.

Other definitions may be adopted for the progression length. It may be expressed relative to the prism reference point or to the far-vision reference point rather than relative to the fitting cross. As the respective positions of these points are moreover also given by the manufacturer, this definition is equivalent to the preceding one.

The inset of the progressive ophthalmic lens is defined as the horizontal shift between the far-vision reference point and the near-vision reference point. The inset E is also called "internal offset".

The behavioral parameter of the individual specifying whether he moves his eyes or his head more during a determined visual task may for example be an eye-head coefficient defined by the ratio of the amplitude of the movement of an eye of the individual in a determined direction in a determined visual situation to the maximum theoretical amplitude of the movement of this eye in this visual situation.

This behavioral parameter may also comprise an amplitude of the movement of at least one eye of the individual and/or an amplitude of the movement of the head of the individual in this determined visual situation.

The determined visual situation may in particular correspond to a reading task.

The eye-head coefficient then for example corresponds to the ratio of the angular amplitude of the movement of the eye of the individual while he is reading a predetermined text to the maximum theoretical amplitude of this movement depending on the width of the text displayed and the reading distance of the individual.

It is possible to compare in the same way the angular amplitude of the movement of the head of the individual while he is reading and the maximum theoretical amplitude of this movement.

Moreover, the average reading distance may be obtained by processing the images obtained in step c), by identifying in these images the image of the reading medium, which belongs to the environment of the individual. It is for example defined as the distance between the rotation centers of the eyes and this reading medium.

The natural posture of the individual at rest corresponds to the position and orientation of the head and of at least said portion of the body of the individual when the latter is not carrying out a particular visual task.

The dynamic behavior of the eyes during the chosen real-life situation is determined using a statistical treatment of the images obtained in step c).

For this purpose a sequence of two- or three-dimensional images is captured in step c) during a predetermined duration. More precisely, at least one sequence of ten images is captured while the movements of the individual are unconstrained.

It is thus possible to deduce therefrom the variation in the sought parameter of visual behavior during this predetermined duration.

The pantoscopic angle of a corrective ophthalmic lens to be placed in a spectacle frame intended to equip the head of the individual is determined so as to decrease the astigmatic aberrations.

Generally, whatever the details of the envisioned implementation, as mentioned above, steps a) and c) may be carried out in the same place, using the same image-capturing device, or in two different places, using two different image-capturing devices.

Preferably, at least steps b) and c) are carried out by the individual in his normal environment.

It is for example envisioned that the normal environment of the user will comprise a working environment, for example a desk; a home environment, for example a sofa placed in front of a television set or an easy chair for reading; and an automobile environment, for example a dashboard equipped with a steering wheel.

The normal environment of the individual also comprises a portion of the neighborhood in which the individual lives.

In the case where it is envisioned to carry out steps a) and c) in the same place, for example the shop of an optician, it is possible for example to envision the first and second image-capturing devices being incorporated into a measuring column located in the shop of the optician.

The column then for example incorporates a device for capturing two-dimensional images, such as a video camera, and a device for capturing three-dimensional images, such as a Kinect or 3D scanner. The two devices may also be combined into a single acquiring system for example using the Ray-light technology.

The device for capturing three-dimensional images may optionally be controlled remotely via a remote control by the optician in order to allow suitable images to be captured in the shop environment, for example while the individual is walking to or reading at one of the dispensing desks thereof.

It is also possible to envision studied placement of a plurality of image-capturing devices, in order to cover the shop environment in its entirety. By way of example, the Kinect has a range of 8 meters over a solid angle of about 60 degrees. It is therefore possible to plan out the places observed by these devices.

It is also possible to envision the first image-capturing device being incorporated into a measuring column, whereas the second image-capturing device comprises a portable device that the optician or individual brings into the shop.

In the case where it is envisioned to carry out steps a) and c) in two different places, for example on the one hand in the shop of an optician and on the other hand in the home of the individual, it is for example possible to envision the first image-capturing device being incorporated into a measuring column located in the shop of the optician and to envision the second image-capturing device being incorporated into a widely available device, that the individual has access to in his home, and which is preferably connectable to the Internet.

In this case, the second measuring device, a Kinect or tablet for example, is connected via an Internet site to the computational processing unit. The individual may identify himself on this site using an identifier and obtain help with the implementation of step c) of the method, for example with the placement of the capturing device, the tests to be carried out before images are captured, etc.

This may be carried out before or after a piece of optical equipment has been sold.

The parameters of visual behavior are used to personalize the ophthalmic lenses intended for the individual. They allow a standard ophthalmic lens to be modified in order to make it match as best as possible the needs of the individual. It is also possible to weight behavioral parameters already determined at the opticians.

The invention claimed is:

1. A method for determining at least one parameter of visual behavior of an individual, comprising the following steps:
   determining the position of the rotation center (CRO) of at least one eye (OD) of the individual in a first frame of reference associated with the head of the individual,
   capturing, using an image-capturing device, at least one image of at least one portion of the body of the individual in a second frame of reference,
   determining the position and orientation, in the second frame of reference, of the first frame of reference associated with the head (TS) of the individual, by seeking the position, in the second frame of reference, of a recognizable zone of said portion of the body of the individual,
   determining the position of the rotation center (CRO) of the eye in the second frame of reference,
   determining the sought parameter of visual behavior.

2. The method as claimed in claim 1, wherein, for the capturing step, the individual is placed in a real-life situation in which the posture of the head (TS) and body of the individual is unconstrained.

3. The method as claimed in claim 1, wherein the position and orientation of the recognizable zone of said portion of the body of the individual are predetermined in the first frame of reference.

4. The method as claimed in claim 1, wherein, in the step of determining the position of the rotation center in the first frame of reference, the position of the rotation center (CRO) of the eye of the individual is determined from a morphological database of the individual.

5. The method as claimed in claim 1, wherein, in the step of determining the position of the rotation center in the first frame of reference, the position of the rotation center (CRO) of the eye of the individual is determined from one or more acquisitions of images of the head (TS) of the individual.

6. The method as claimed in claim 1, wherein, in the capturing step, said image is a three-dimensional representation of the portion of the body of the individual.

7. The method as claimed in claim 1, wherein, in the capturing step, said image is a three-dimensional representation of the head of the individual.

8. The method as claimed in claim 1, wherein, in the capturing step, a sequence of images is captured during a predetermined duration, and, in the step of determining the sought parameter of visual behavior, the variation in the sought parameter of visual behavior during this predetermined duration is deduced therefrom.

9. The method as claimed in claim 1, wherein, in the step of determining position and orientation, said recognizable zone consists of a pinpointing system mounted on the head (TS) of the individual, of a spectacle frame (10) placed on the head (TS) or of one or more recognizable points of the face of the individual.

10. The method as claimed in claim 1, wherein, in the step of determining the parameter of visual behavior, the direction of the gaze of the individual in said real-life situation is determined, and a zone of use of the ophthalmic lens corresponding to this real-life situation is determined therefrom.

11. The method as claimed in claim 10, wherein, to determine the direction of the gaze of the individual, the image of the pupil of the individual is identified in the image captured in the capturing step, and the sought direction of the gaze is deduced therefrom depending on the position of the rotation center (CRO) in the first frame of reference, said position being determined in the step of determining the position of the rotation center in the first frame of reference.

12. The method as claimed in claim 10, wherein, to determine the direction of the gaze of the individual, the position in the second frame of reference of elements targeted by the gaze and belonging to the environment of the individual is determined.

13. The method as claimed in claim 12, wherein, said elements targeted by the gaze are displayed on an electronic screen and have a known position with respect to the image-capturing device.

14. The method as claimed in claim 1, wherein, in the step of determining the position of the rotation center in the first frame of reference,
at least two images of the head (TS) of the individual are captured using an image-capturing device, in which images the postures of the head (TS) of the individual with respect to this image-capturing device are different and in which images the individual is fixating his gaze on a sighting point of predetermined position,
the gaze directions of the individual corresponding to each of the two images are determined,
the position of the rotation center (CRO) of the eye of the individual is deduced therefrom.

15. The method as claimed in claim 1, wherein, in the step of determining the position of the rotation center in the first frame of reference, the head (TS) of the individual is equipped with a pair of spectacles surmounted by a pinpointing system, in the capturing step, the captured portion of the body comprises the head (TS) of the individual equipped with this pinpointing system, and, in the step of determining the position and orientation, the recognizable zone consists of this pinpointing system.

16. The method as claimed in claim 1, wherein the sought parameter of visual behavior of the individual is one of the following:
a zone of use corresponding to the real-life situation of step b) for a corrective lens to be placed in a spectacle frame (10) intended to equip the head of the individual,
a behavioral parameter of the individual specifying whether he moves his eyes or head (TS) more,
average reading distance,
natural posture of the individual at rest,
dynamic behavior of the eyes during the chosen real-life situation,
position of a near-vision zone or progression length or inset of a corrective lens to be placed in a spectacle frame (10) intended to equip the head (TS) of the individual,
the pantoscopic angle of a corrective lens to be placed in a spectacle frame (10) intended to equip the head (TS) of the individual determined so as to decrease the astigmatic aberrations.

17. The method as claimed in claim 1, wherein the steps of determining the position of the rotation center in the first frame of reference and of capturing are carried out in one and the same place, using one and the same image-capturing device.

18. The method as claimed in claim 1, wherein the steps of determining the position of the rotation center in the first frame of reference and of capturing are carried out in two different places, using two different image-capturing devices.

19. The method as claimed in claim 2, wherein the position and orientation of the recognizable zone of said portion of the body of the individual are predetermined in the first frame of reference.

20. The method as claimed in claim 2, wherein, in the step of determining the position of the rotation center in the first frame of reference, the position of the rotation center (CRO) of the eye of the individual is determined from a morphological database of the individual.

* * * * *